United States Patent [19]

Sersen

[11] Patent Number: 5,067,353
[45] Date of Patent: Nov. 26, 1991

[54] ROOF SHEATHING TEST SYSTEM

[76] Inventor: Stanley J. Sersen, 1138 Valley Dr., Pasadena, Md. 21122

[21] Appl. No.: 674,959

[22] Filed: Mar. 26, 1991

[51] Int. Cl.$^5$ .............................................. G01N 3/20
[52] U.S. Cl. ...................................................... 73/849
[58] Field of Search ................. 73/786, 852, 849, 851, 73/853, 818, 788

[56] References Cited

FOREIGN PATENT DOCUMENTS

| 1288520 | 2/1987 | U.S.S.R. | 73/786 |
| 2148517 | 5/1985 | United Kingdom | 73/849 |

*Primary Examiner*—Jerry W. Myracle
*Attorney, Agent, or Firm*—Morton J. Rosenberg; David I. Klein

[57] ABSTRACT

A roof sheathing test system (10) is provided which may be manually operated and is substantially non-destructive in nature for load and deflection testing of roof sheathing (12). The roof sheathing test system (10) includes a test frame (14) which is mounted to a pair of displaced roof structural members (16). The roof sheathing test system (10) is mounted to the roof structural members (16) by a foot member (30) which is fixedly secured to the roof structural members (16) and the foot member (30) is releasably secured to the overall test frame (14). A load cell system (52) is secured to the test frame (14) for registering a force load applied to the sheathing (12). A load base mechanism (72) is in contact with the load cell system (52) and an upper surface of the sheathing (12). Rotation of a threaded rod (82) located within a load base rod member (76) is rotated to apply a force to the sheathing (12) which is registered on a load cell gauge (54). Indicia (88) formed on an external surface of the load base rod member (76) provides for a visual registering of the deflection of the sheathing (12) as a load is applied. In this manner, there is provided a roof sheathing test system (10) which is manually operated and removable from the roof subsequent to operational tests.

20 Claims, 3 Drawing Sheets

ROOF SHEATHING TEST SYSTEM

BACKGROUND OF THE INVENTION

1. Field of the Invention

This invention is directed to both a method and system for testing roof sheathings. In particular, this invention relates to a roof sheathing test system and method which is manually operated and may be easily attached and removed from a roof being tested. Still further, this invention directs itself to a roof sheathing test system which allows fixed securement of a portion of the test system to the roof being tested while a test frame is removably secured for the operational tests. More in particular, this invention is directed to a system where a particular loading is applied to the sheathing of a roof for determination of the strength of the roof sheathing. Additionally, this invention is related to a system whereby the deflection at differing load values may be registered in a simple, economical manner during the operational phase of the testing. Further, this invention directs itself to a roof sheathing test system which tests according to the U.S. Product standards provided by the American Plywood Association Rules and Regulations. Further, this invention relates to a roof sheathing test system which may be easily brought to a test site to apply the operational test in an effective, low cost, non destructive, manner.

2. Prior Art

Test systems for measuring load and deflections are known in the art. The best prior art known to the Applicant includes U.S. Pat. Nos. 4,589,288; 4,213,349; 2,854,847; 4,747,314; 3,194,063; 3,533,283; 3,942,362; 3,041,873; 4,300,398; 4,543,126; 3,443,423; and, 4,289,047.

In some prior art, such as that shown in U.S. Pat. No. 4,589,288 there is provided a device for non-destructive testing of wood panels. In such prior art systems a force load is applied to a wood panel through a force applying assembly having a loading bar which is coupled thereto. The force applying assembly provides a known displacement to the panel by virtue of its predetermined stroke and a load cell provides monitoring of the applied force. However, such prior art systems do not provide for a simple and effective non-destructive load testing system where there is a combination of fixed securement to the roof truss members and a releasable securement to the test frame in the manner shown by the subject Patent Application system and method. Additionally, such prior art systems do not provide for the particular method and mode of operation whereby the force loading and the deflection of the sheathing may be provided during the test operation in the manner shown by the subject Patent Application system.

In other prior art systems, such as that shown in U.S. Pat. No. 4,213,349, there are testing machines to determine the stiffness of a test specimen. Such does provide a screw jack arrangement to apply force to a specimen under test and is measured by some type of dial gauge interposed therebetween. The force applying assembly may be supported by a pair of vertical legs in such prior art systems however the specimens are disposed between the force applying member and a crossbar which is not part of the combination of elements nor workable in the particular operational system as described herein.

SUMMARY OF THE INVENTION

This invention directs itself to a roof sheathing test system and method which includes a test frame mounted to at least a pair of roof truss members. The test system further includes a mechanism for mounting the test frame to the roof truss members and a load cell is coupled to the test frame member for registering a force load applied to the sheathing. A mechanism is provided for applying the force load to the sheathing and there is a further mechanism for measuring a deflection of the sheathing responsive to the force load applied to the sheathing.

DESCRIPTION OF THE PREFERRED EMBODIMENTS

Figure 1:
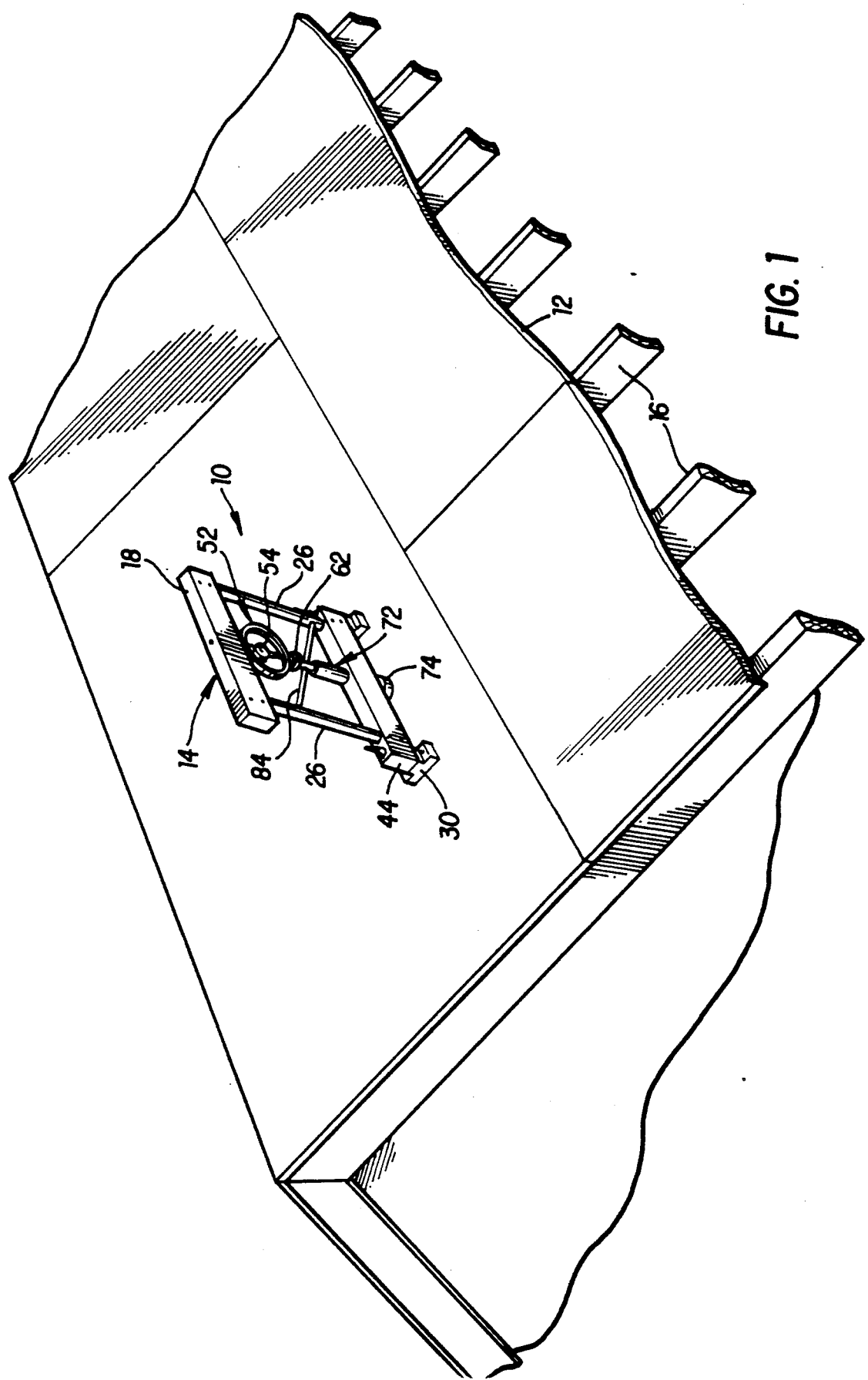
FIG. 1 is a perspective view partially in cut away of the roof sheathing test system of the instant invention showing the roof sheathing test system mounted on the roof of a building.

Referring now to FIGS. 1-5 there is shown roof sheathing test system 10 for load testing roof sheathing 12. In overall concept, roof sheathing test system 10 is used for applying a load to roof sheathing 12 in the normal environment of roof sheathing 12 mounted on a roof of an edifice. Additionally, as well as force load readings being taken, roof sheathing test system 10 as will be seen in following paragraphs allows for the measuring of a deflection of sheathing 12 responsive to a force load applied to sheathing 12.

In particular, roof sheathing test system 10 is designed to determine whether the strength of fire retardant treated plywood meets current U.S. Product Test standards as developed by the American Plywood Association. American Plywood Association test procedures provide for concentrated load testing as a method of determining the strength of sheathing 12. The subject roof sheathing test system 10 was developed to be a lightweight device that may be manually and easily handled in the field in the environment of use. System 10 is mounted to the exterior of roof sheathing 12 and applies a load in a downward manner to test the strength of the material. System 10 is specifically designed to allow set-up and operation manually by a user.

Roof sheathing test system 10 includes test frame 14 mounted to at least a pair of roof truss members 16 during operation via foot members 30. Test frame 14 includes upper frame member 18 extending in longitudinal direction 20. Lower frame member 22 extends in longitudinal direction 20 and is displaced from upper frame member 18 in vertical direction 24. Vertically extending post members 26 are longitudinally displaced each from the other and fixedly secured to upper and lower frame members 18 and 22 on opposing ends of post members 26.

Figure 2:
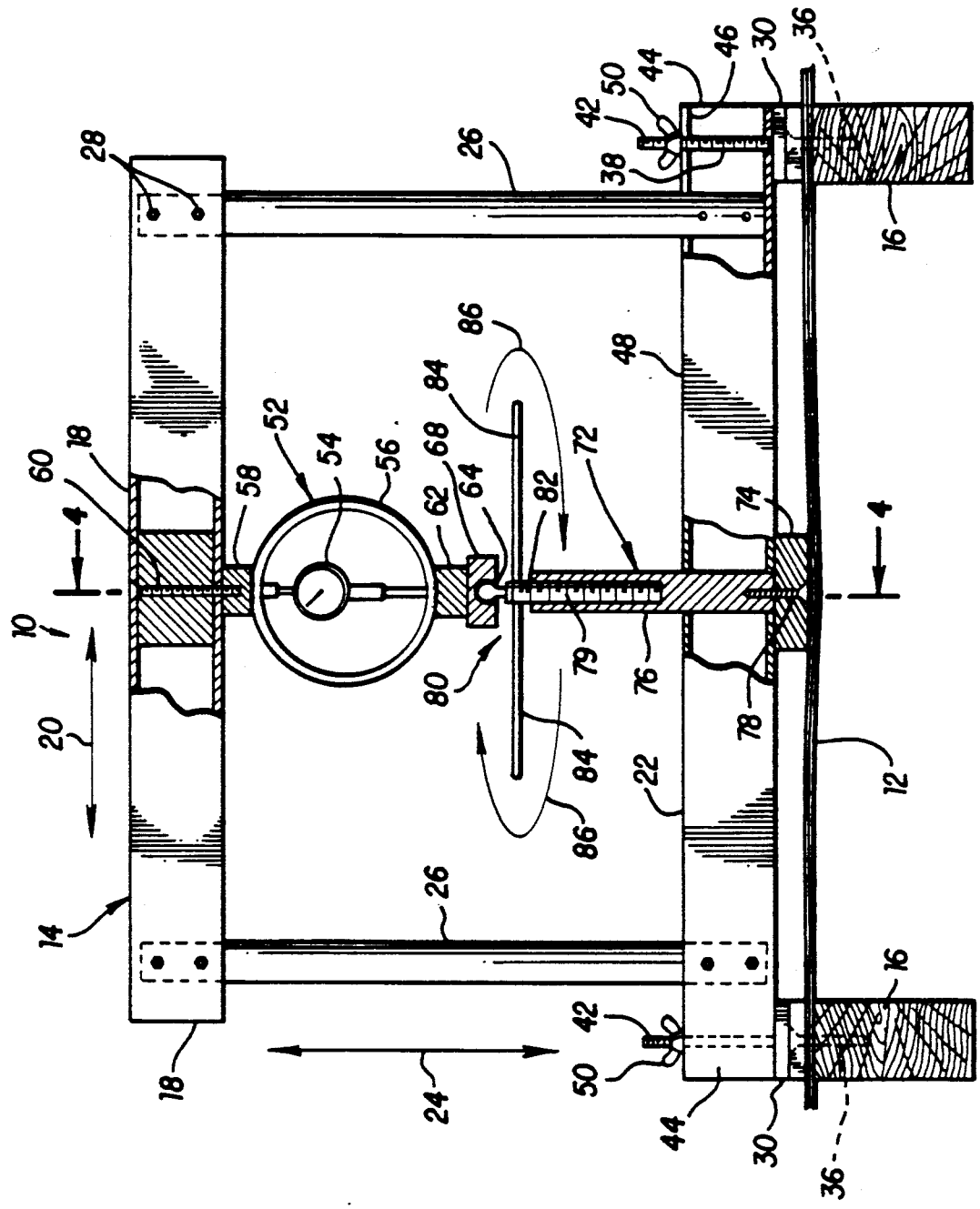
FIG. 2 is an elevational view of the roof sheathing test system partially cutaway and in cross-section to show the operating mechanisms of the subject invention concept.

As can be seen in FIGS. 1 and 2, upper frame member 18 and lower frame member 22 are generally parallel each to the other in final construction. Opposing post members 26 are rigidly secured to upper frame member 18 and lower frame member 22 through threaded bolts 28 or some like securement not important to the inventive concept as herein described with the exception that post members 26 be fixedly secured in rigid fashion to upper and lower frame members 18 and 22.

In further overall construction, test frame 14 takes the general contour of a rectangular or square shape with frame members 18,22 and post members 26 being formed of steel or some like rigid material which can accept the loads imposed thereon and maintain its structural integrity.

Figure 3:
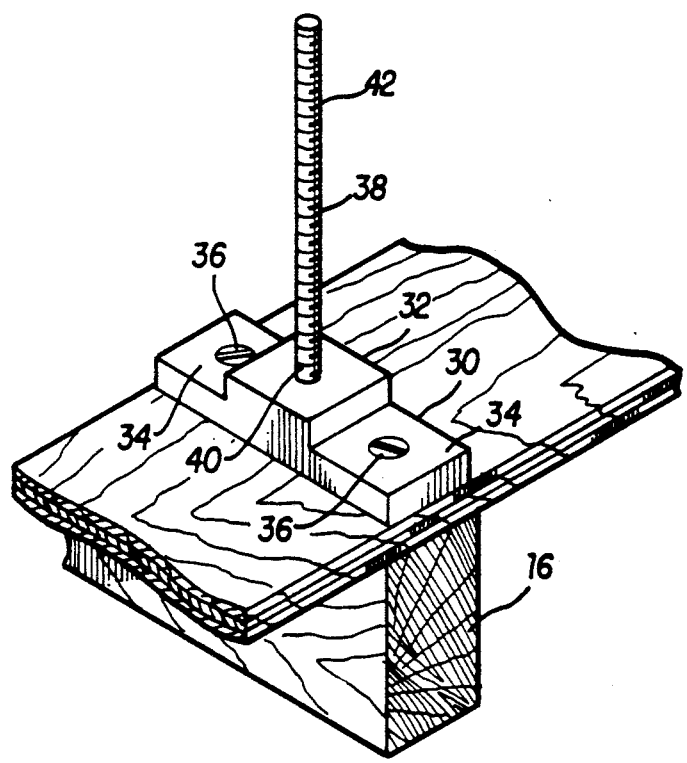
FIG. 3 is a perspective view of the fixed securement portion of the roof sheathing test system mounted to a roof truss member.

Roof sheathing test system 10 further includes a mechanism for mounting test frame 14 to roof truss members 16. The particular mechanism for mounting test frame 14 includes a pair of foot members 30 clearly shown in FIGS. 1, 2, 3 and 5. As seen in FIG. 3, foot members 30 include a stepped contour having a centrally raised section 32 and opposing end sections 34 secured in rigid fashion to roof truss member 16.

In operation, end sections 34 are fixedly secured to roof truss members 16 by screws, bolts, nails or some like securement 36. In this manner, foot members 30 are rigidly secured to roof truss members 16 during the operation of the load testing performed by roof sheathing test system 10.

Further referring to FIG. 3, mounting rod member 38 extending in vertical direction 24 is fixedly secured to foot member 30 on first end 40 of mounting rod member 38. Mounting rod member 38 includes threaded second end 42 as shown. The vertical length of mounting rod member 38 must be greater than the vertical dimension of lower frame member 22 for purposes to be discussed in the following paragraph. Mounting rod member 38 is formed of steel or some like material which has sufficient diameter to accept the loads imparted thereon. Additionally, mounting rod first end 40 is mounted to foot member 30 through welding or some like rigid fastening method. Foot member 30 may be also formed of steel or some like material having a high force load acceptability range.

Figure 5:
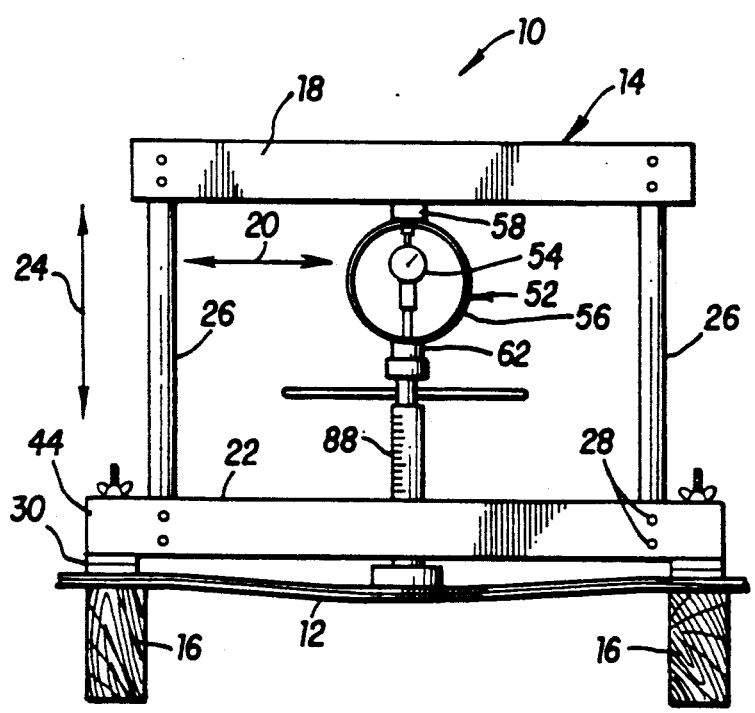

As seen in FIGS. 2 and 5, lower frame member 22 extends in longitudinal direction 20 beyond said post members 26 for providing securement sections 44 adapted to be releasably secured to foot member 30. As clearly seen in FIG. 2, lower frame member 22 has a larger longitudinal dimension than upper frame member 18.

Mounting rod member 38 is releasably securable to lower frame member 22 at securement sections 44. Lower frame member 22 includes vertically directed through openings 46 for passage therethrough of rod members 38 as is seen in FIG. 2. Mounting rod member 38 extends through lower frame member 22 and above lower frame member upper surface 48 defining second end 42 of mounting rod member 30. Wing nut 50 is threadedly secured to mounting rod member threaded second end 42 in order to provide for releasable securement of foot member 30 to lower frame member 22.

In this manner, overall test frame 14 may be fixedly secured to a roof or roof truss members 16 during operation of the load testing.

Roof sheathing test system 10 further includes load cell mechanism 52 for measuring the force loading on roof sheathing 12 during operation of test system 10. Load cell system 52 may be a standard off-the-shelf load cell purchased from Soil Test Inc. located in Lake Bluff, Ill., having a Model #PR-05.

Load cell system 52 includes load cell outer frame 56 which is fixedly attached to load cell upper frame block member 58. Load cell bolt member 60 passes through upper frame member 18 and threadedly engages load cell upper cell block member 58 to maintain load cell system 52 in a fixed securement mode to test frame 14 and in particular to upper frame member 18 during operation of the test system 10.

Figure 4:
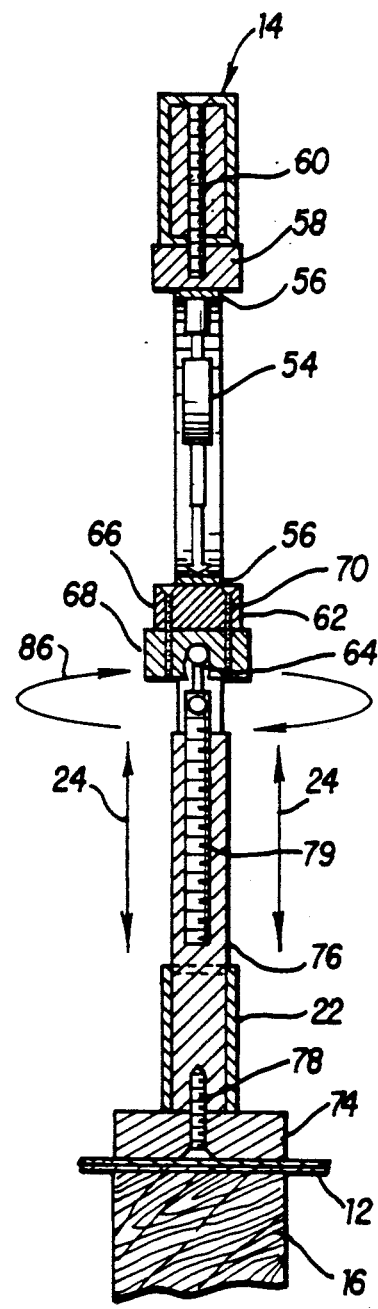
FIG. 4 is a cross-sectional view of the roof sheathing test system taken along the cross-section line 4—4 of FIG. 2; and, FIG. 5 is an elevational view of the roof sheathing test sytem showing a deflection of the roof sheathing under an applied load.

Load cell bolt member 60 as seen in FIG. 2 passes through upper frame member 18 and is threadedly secured to load cell upper block member 58 which may be welded or otherwise fixedly secured to load cell outer frame 56. Load cell lower block 62 is fixedly secured to load cell outer frame 56 by welding or some like technique not important to the inventive concept as herein described with the exception that load cell lower block 62 be fixedly secured to load cell outer frame 56. Load cell lower block member 62 includes a recess or well 64 as is clearly seen in FIG. 2. As shown in FIG. 4, load cell lower block 62 may be formed of two discrete blocks 66 and 68 coupled each to the other through threaded bolt member 70. Alternatively, load cell lower block 62 may be a singular block member formed in one-piece formation.

Roof sheathing test system 10 includes a mechanism for applying force load to sheathing 12. The mechanism for applying a force load to sheathing 12 includes load base mechanism 72 shown clearly in FIGS. 2 and 5 extending through lower frame member 22. Load base mechanism 72 is vertically displaceable with respect to lower frame member 22. Load base mechanism 72 includes load base disc or foot member 74 shown in FIG. 2 which is captured between an upper surface of roof sheathing 12 and a lower surface of lower frame member 22. Load base mechanism 72 further includes vertically extending load base rod member 76 which is fixedly secured to load base disc member 74 through bolt 78 at a lower end thereof. Vertically extending load base rod member 76 passes vertically through lower frame member 22 and is displaceable with respect to lower frame member 22 as is clearly seen in FIG. 5 where sheathing 12 has been deformed. Load base rod member 76 further includes internally threaded opening 79 formed in an upper end thereof seen in FIG. 2. Further shown in FIG. 2 is mechanism 80 for vertically displacing load base mechanism 72 in reversible vertical direction 24. Vertical displacement mechanism 80 includes threaded rod 82 which threadedly engages the internal threaded opening 79 in the upper end of load base rod member 76. Threaded rod 82 is in releasable contact with load cell lower block 62 through a ball and joint connection as shown in FIG. 2. In this manner threaded rod 82 is in releasable and displaceable contact with load cell system 52. Additionally, there is provided extendable members 84 extending radially from threaded rod 82 to be used to provide rotation of threaded rod 82 in the direction shown by directional arrows 86. In this manner there is provided a mechanism for rotating threaded rod 82 in a plane substantially normal vertical direction 24.

Indicia 88 are formed on load base rod member 76 as is shown in FIGS. 1 and 5. Indicia 88 provide a mechanism for measuring the deflection of sheathing 12. Indicia 88 is formed on an external surface of load base rod member 76 and as can be seen in FIG. 5 when extendable members 84 are rotated to provide a predetermined force applied by load base disc or foot member 74 on sheathing 12, an upper surface 48 of lower frame 22 is relatively displaced with respect to indicia 88. During an initial operation, the indicia 88 may be read and after a predetermined load is placed on sheathing 12 by rotation of extendible members 84, a second indicia reading may be read to provide a difference and obtain a deflection reading for the predetermined load being applied to sheathing 12.

The overall method of testing roof sheathing 12 includes the step of mounting test frame 14 on a pair of longitudinally displaced roof truss members 16. Load cell system 52 is fixedly secured to test frame 14 for registering a force load applied to sheathing 12. A force load is applied to sheathing 12 and there is a simultaneous measuring of the force load applied to the sheathing 12 and a vertical deflection of the sheathing 12 responsive to the applied force load.

The general step of mounting test frame 14 includes the steps of fixedly securing foot member 30 to truss member 16 and then releasably securing test frame 14 to foot member 30.

Foot member 30 is secured to truss members 16 in a fixed securement mode through nailing or bolting and includes mounting rod member 38 passing in vertical direction 24.

Mounting rod member 38 is inserted through lower frame member 22 in one portion thereof and rod 38 is threadedly secured to lower frame member 22 by nut member 50.

The step of applying a force load to roof sheathing 12 includes the step of fixedly securing load cell system 52 to upper frame member 18 through bolting or some like rigid securement method. Additionally, load cell system 52 is vertically aligned with load base mechanism 72 in a somewhat displaceable manner through a ball in joint type socket formed within load cell lower block 62.

The step of applying a force load to sheathing 12 further includes manually rotating extendable members 84 in a direction 86 wherein extendable members 84 are fixedly secured to threaded rod 82 rotatively mounted within internal threaded opening 79 of load base rod member 76.

As extendable members 84 are rotated, load base rod member 76 applies a force through load base disc member 74 to sheathing 12 and a deflection occurs responsive to the applied force loading.

The force load may be read directly from load cell gauge 54 and the deflection of sheathing 12 is read by the difference in indicia 88 formed on an external surface of load base rod member 76.

The subject roof sheathing test system and method is generally applicable to product standards developed by the American Plywood Association Test Procedures as seen in the U.S. Product Standard. In particular, the subject system and method was developed to be a lightweight device which may be easily handled in field applications and is applied to exterior roof sheathing 12 to apply a load downward to test the strength of the material and provide a 400 pound load onto the roof to see if failure is found. Additionally, there is provided a test for deflection under a 200 pound load which directs itself to certain product standards provided by the American Plywood Association.

An overall roof sheathing procedure is completed through a plurality of operations. Initially, the inside of the roof is inspected by the operator entering the interior of the building and looking for deteriorated material.

Subsequent to this step, the operator will go external the building and system 10 may be positioned in a few prime locations. Generally two areas on a panel near the eave edge are located and tested. The system 10 is manually carried to the roof and structural supports 16 are located. Detachable feet 30 are fixedly secured to structural members 16. Typically, drywall screws or nails 36 may be drilled through shingles into the top of truss members or rafters 16.

Detachable feet 30 are attached to the roof and system 10 is secured to foot member 30 through insertion of threaded rod members 38 through lower frame members 22.

Once secured by wing nuts 50, test frame 14 is fixed in place and ready for the testing. Extendable members 84 are rotated and load base disc member 74 which is generally a three inch diameter disk is brought into contact with the roof surface. Once disk 74 is in contact with roof surface, a mark is made on calibrated vertical rod 76 or notation of a particular indicia 88 is made.

The initial indicia 88 reading is a zero point for the test. Additionally, gauge 54 is zeroed on load cell system 52.

Extendable members 84 are then rotated and generally manually rotated at a speed of approximately 100 pounds per 30 seconds in accordance with American Plywood Association standards.

Once a reading of 200 pounds of force is seen on gauge 54, the deflection reading of sheathing 12 is noted. The loading of the roof is continued at the rate of 100 pounds per 30 seconds until a reading of 400pounds of load is seen on gauge 54. Once the 400 pound load is seen, the total deflection of the sheathing 12 is noted from indicia 88.

Obviously, if the 400 pound loading is not reached, the roof fails and the maximum amount of loading remains visually seen on gauge 54. When the roof fails, fibers crack and force loading to the roof may not be increased.

Once the operation has been completed, system 10 is removed from the roof and measurements of deflection are read and recorded.

Subsequent to removal of system 10 from the roof, shingle tabs are lifted and the holes made are sealed with roofing cement compound and the shingles are then laid down and cemented to prevent any possible leakage.

The overall test procedure is substantially a nondestructive test in accordance with American Plywood Association rules and regulations.

Although this invention has been described in connection with specific forms and embodiments thereof, it will be appreciated that various modifications other than those discussed above may be resorted to without departing from the spirit or scope of the invention. For example, equivalent elements may be substituted for those specifically shown and described, certain features may be used independently of other features, and in certain cases, particular locations of elements may be reversed or interposed, all without departing from the spirit or scope of the invention as defined in the appended claims.

What is claimed is:

1. A roof sheathing test system comprising:
   (a) a test frame mounted to at least a pair of roof structural members;
   (b) means for mounting said test frame to said roof structural members;
   (c) a load cell coupled to said test frame member for registering a force load applied to said sheathing;
   (d) means for applying said force load to said sheathing; and,
   (e) means for measuring a deflection of said sheathing responsive to said force load applied to said sheathing.

2. The roof sheathing test system as recited in claim 1 where said test frame includes:
   (a) an upper frame member extending in a longitudinal direction;
   (b) a lower frame member extending in said longitudinal direction and displaced from said upper frame member in a vertical direction;
   (c) a pair of vertically extending post members, longitudinally displaced each from the other and fixedly secured to said upper and lower frame members on opposing ends of said post members.

3. The roof sheathing test system as recited in claim 2 where said means for mounting said test frame to said roof structural members includes:
   (a) at least one foot member fixedly secured to said roof structural member; and,
   (b) a mounting rod member extending in said vertical direction, said mounting rod member being fixedly secured to said foot member on a first end thereof.

4. The roof sheathing test system as recited in claim 3 where said mounting rod member is releasably securable to said lower frame member.

5. The roof sheathing test system as recited in claim 3 where said lower frame member includes at least one vertically directed through opening for passage therethrough of said mounting rod member.

6. The roof sheathing test system as recited in claim 5 where said mounting rod member extends through said lower frame member and above an upper surface of said lower frame member defining a second end of said mounting rod member.

7. The roof sheathing test system as recited in claim 6 where said second end of said mounting rod member is threaded for engagement of a cooperating nut member for releasably securing said foot member to said lower frame member.

8. The roof sheathing test system as recited in claim 7 where said lower frame member extends in said longitudinal direction beyond said post members for providing a securement section adapted to be releasably secured to said foot member.

9. The roof sheathing test system as recited in claim 2 where said means for applying said force load to said sheathing includes:
   (a) load base means extending through said lower frame member for being vertically displaceable with respect thereto; and,
   (b) means for vertically displacing said load base means and simultaneously applying a force load to said load cell.

10. The roof sheathing test system as recited in claim 9 where said load base means includes:
    (a) a load base disc member captured between an upper surface of said roof sheathing and a lower surface of said lower frame member; and,
    (b) a vertically extended load base rod member fixedly secured to said load base disc member at a lower end thereof and passing through said lower frame member.

11. The roof sheathing test system as recited in claim 10 where said load base rod member includes an internally threaded opening formed in an upper end thereof.

12. The roof sheathing test system as recited in claim 11 where said means for vertically displacing said load base means includes:
    (a) a threaded rod for threadedly engaging said internal threaded opening in said upper end of said load base rod member, said threaded rod being in releasable contact with said load cell; and,
    (b) means for rotating said threaded rod in a plane substantially normal said vertical direction.

13. The roof sheathing test system as recited in claim 12 where said means for rotating said threaded rod includes a rod member extending from said threaded rod for manual rotation thereof.

14. The roof sheathing test system as recited in claim 12 where said threaded rod is displaceably mounted to said load cell.

15. The roof sheathing test system as recited in claim 14 where said threaded rod displaceable mounting includes a ball joint connection to said load cell.

16. The roof sheathing test system as recited in claim 15 where said load cell is fixedly coupled to said upper frame member.

17. The roof sheathing test system as recited in claim 10 where said means for measuring said deflection of said sheathing includes indicia means formed on an external surface of said vertically extended load base rod member.

18. A method of testing a roof sheathing including the steps of:
    (a) mounting a test frame to at least a pair of longitudinally displaced roof structural members;
    (b) establishing a load cell mounted to said test frame for registering a force load to said sheathing;
    (c) applying a force load to said sheathing; and,
    (d) simultaneously measuring (1) said force load applied to said sheathing, and (2) a vertical deflection of said sheathing responsive to said applied force load.

19. The method of testing a roof sheathing as recited in claim 18 where the step of mounting a test frame includes the steps of:
    (a) fixedly securing at least one foot member to at least one truss member, and,
    (b) releasably securing said test frame to said foot member.

20. The method of testing a roof sheathing as recited in claim 18 where the step of applying a force includes the step of displaceably coupling said load cell to a vertically displaceable load base rod member, said load base rod member being vertically displaceable responsive to said force load applied to said sheathing.

* * * * *